US00PP11540P

United States Patent [19]

Olesen et al.

[11] Patent Number: Plant 11,540

[45] Date of Patent: Oct. 3, 2000

[54] FLORIBUNDA ROSE PLANT NAMED 'POULMANTI'

[75] Inventors: L. Pernille Olesen; Mogens N. Olesen, both of Fredensborg, Denmark

[73] Assignee: Poulsen Roser ApS, Fredensborg, Denmark

[21] Appl. No.: 09/140,631

[22] Filed: Aug. 26, 1998

[51] Int. Cl.[7] ..... A01H 5/00

[52] U.S. Cl. ..... Plt./149

[58] Field of Search ..... Plt./102, 107, 141, Plt./148, 149

*Primary Examiner*—Howard J. Locker

[57] ABSTRACT

A new compact floribunda rose plant which has abundant, non-fading, pink flowers. The variety successfully propagates from softwood cuttings and is suitable for year round production in commercial glasshouses and nurseries. This new and distinct variety has shown to be uniform and stable in the resulting generations from asexual propagation.

1 Drawing Sheet

SUMMARY OF THE DISCOVERY

The present discovery constitutes a new and distinct variety of a floribunda rose plant which was discovered in a cultivated area. The mutation resulted from 'POULskov', a floribunda rose hybridized by the same inventors. 'POULskov' is described and illustrated in U.S. Plant Pat. No. 9,062 and issued on Feb. 28, 1995. The new rose variety resulted from a naturally occurring mutation of unknown causation on a branch of 'POULskov'.

The rose plant of the present discovery has a unique combination of characteristics which are outstanding in the new variety and which distinguish it from the original rose 'POULskov' as well as all other varieties which we are aware of. For example, the new variety has:

1. Abundant, pink, very double flowers;
2. Vigorous and compact growth,
3. Year-round flowering under glasshouse conditions;
4. Suitability for production from softwood cuttings in pots;
5. Durable flowers and foliage which make the variety suitable for distribution in the floral and nursery industry.

This combination of qualities was not present in previously available commercial cultivars in this market class and distinguish 'POULmanti' from all other varieties of which we are aware.

The mutation was selected and evaluations were conducted on the resulting rose plants in a controlled environment.

Asexual reproduction of 'POULmanti' by cuttings was first done by L. Pernille and Mogens N. Olesen in their nursery in Fredensborg, Denmark in April, 1996. This initial and other subsequent propagations have demonstrated that the characteristics of 'POULmanti' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, stems, and a plant of 'POULmanti'. Specifically illustrated in Sheet 1:

1. Stem or entire plant showing branching and the attachment of leaves, buds, and peduncles;

2. Flower bud, partially opened bud, and open bloom;

3. Flower petals, detached;

4. Sepals, receptacle, and pedicel;

5. Flowering stem as well as a bare stem exhibiting thorns;

6. Leaves.

DETAILED DESCRIPTION OF THE VARIETY

The following is a detailed description of 'POULmanti' as observed in its growth in glasshouses in Fredensborg, Denmark and Burlington, Canada; and in a field nursery in Jackson County, Oreg. Color references are made using The Royal Horticultural Society (London, England) Colour Chart, 1995, except where common terms of color are used.

For a comparison, several physical characteristics of the rose variety 'POULskov', a patented rose variety from the same inventors described and illustrated in U.S. Plant Pat. No. 9,062 and issued on Feb. 28, 1995 are compared to 'POULmanti' in Chart 1.

CHART 1

| | 'POULmanti' | 'POULskov' |
|---|---|---|
| Bud color | Red-Purple Group 57C | Red Group 55D–56A |
| Color, flower petal, upper surface | Red Group 55A | Red Group 49D–56B |
| Color, flower petal, reverse surface | Red-Purple Group 57C–68A | Red Group 55D-56A |

Parents: Mutation of 'POULskov'.

Classification:

*Botanical.*—*Rosa hybrida.*

*Commercial.*—Floribunda.

FLOWER AND FLOWER BUD

Blooming cycle: Nearly continuous.

Flower bud:

*Size.*—Upon opening, 20 mm–25 mm in length from base of receptacle to flower tip.

*Bud form.*—Ovoid to globular.

*Bud color.*—Red-Purple Group 57C at ¼ opening.

*Sepals.*—*Green Group* 137C. Some sepals with feathered foliaceous appendages at tips of sepals, otherwise appendages generally lacking. Surfaces of some sepals lightly pubescent.

*Peduncle.*—Surface: Above average number of stipitate glands present. Length: 25 mm–45 mm. Color: Green Group 138A. Most peduncles with coloration of Greyed-Purple Group 183B. Strength: Erect and upright.

*Receptacle.*—Surface: Smooth, glabrous. Shape: Urn-shaped. Size: Medium. 6 mm (h)×6 mm (w). Color: Green Group 138A.

*Borne.*—Generally 1–4 buds per flowering stem.

Flower bloom:

*Size.*—Average flower diameter is 60 mm when open.

*Form.*—Shape of flower when viewed from the side: Upon opening, upper part: Convex to flattened convex. Upon opening, lower part: Flattened convex. Open flower, upper part: Convex. Open flower, lower part: Concave to flat.

*Petals.*—Generally straight, some weakly reflexed.

*Petalage.*—Very double. Average range: 40–50 under normal conditions with 5–10 petaloids.

Color:

*Upon opening, petals.*—Upper Surface: Red Group 55A. Reverse Side: Red-Purple Group 57C–68A.

*Upon opening, basal petal spot.*—Outermost petals: Outer Side: Yellow Group 9D. Inner Side: Yellow Group 9C. Innermost petals: Outer Side: Yellow Group 9C. Inner Side: Yellow Group 9C.

*After opening, petals.*—Outermost petals: Upper Surface: Red Group 55B–55C. Reverse Side: Red-Purple Group 68C. Innermost petals: Upper Surface: Red Group 55A–62A. Reverse Side: Red-Purple Group 57D.

*After opening, basal petal spots.*—Outermost petals: Outer Side: Yellow Group 9D. Inner Side: Yellow Group 9D. Innermost petals: Outer Side: Yellow Group 9D. Inner Side: Yellow Group 9C.

General Tonality: No change in the general tonality at the end of the third day. Afterwards, general tonality is Red Group 55B–55C.

Petals:

*Petal reflex.*—Petals reflex backwards slightly. Some outside petals double reflexed.

*Petal edge.*—Uniform.

*Petaloids.*—Present. Quantity: 5–10.

*Fragrance.*—Light.

*Duration.*—As a pot plant, flowers last from 8 to 10 days. As a cut flower 6 to 8 days.

*Texture.*—Moderately heavy.

*Shape.*—Outermost petals generally round. Innermost petals more narrow.

*Arrangement.*—Regular.

Reproductive organs:

*Pollen.*—Color: Greyed-Yellow Group 162B. Abundance: Average.

*Anthers.*—Size: Small-Medium. Color: Early, Yellow-Orange Group 16B, changing to Greyed-Orange Group 164B. Abundance: Average.

*Filaments.*—Color: Green-White Group 157B.

*Stigmas.*—Slightly superior in location to anthers. Color: Green-White Group 157C.

*Styles.*—Color: Green-White Group 157C.

PLANT

Plant growth: Vigorous, compact, upright to bushy with full branching. When grown as a 15 cm pot plant, the average height of the plant itself is 22–25 cm and the average width is 24 cm. When grown as a nursery plant on its own roots, the average plant height is 60–75 cm and the average width is 55–65 cm.

Stems:

*Color.*—Young wood: Green Group 138B. Older wood: Green Group 138B.

*Prickles.*—Incidence: Moderately thorny. Size: Average length: 5 mm–6 mm. Color: Green Group 145D to Yellow Group 154D. Thorns on plants grown in full sun exhibit intonations of Greyed-Red Group 180A. Shape: Linear to curved downward.

*Bark.*—Young wood: Smooth. Older wood: Smooth.

Plant foliage: Normal number of leaflets on normal leaves in middle of stem: 5 leaflets. Some leaves with 7 leaflets, the two lowermost leaflets generally much reduced in size.

*Leaf size.*—Medium. Average size=90 mm (l)×60 mm (w).

*Abundance.*—Very abundant.

*Color.*—Upper Leaf Surface: Green Group 137A to 139A. Lower Leaf Surface: Green Group 138B. Juvenile foliage: Upper Leaf Surface: Green Group 137B–137C with intonations of Greyed-Purple Group 183B. Lower Leaf Surface: Green Group 138B with little to no greyed-purple intonations.

Plant leaves and leaflets:

*Stipules.*—Present. Size: Small. 8 mm–12 mm. Color: Green Group 137A–139B.

*Petiole.*—Length: 15 mm to 25 mm. Underneath: Without prickles or stipitate glands. Color: Green Group 137C.

*Rachis.*—With one or two small prickles underneath. Color: Green Group 137C. Outdoor grown plants with intonations on upper surface of Greyed-Purple Group 183B.

*Leaflet.*—Edge: Serrated. Shape: Leaflets are ovate to round.

*Other.*—Moderately glossy surface. Moderately thick texture.

Disease resistance: Above average resistance to powdery mildew and Botrytis under normal growing conditions in glasshouses in Burlington, Canada. Above average resistance to blackspot and powdery mildew in field nursery in Jackson County, Oreg.

We claim:

1. A new and distinct variety of rose plant of the floribunda class, substantially as herein illustrated and described as a distinct and novel rose variety due to its abundant pink flowers, vigorous and compact growth, year round flowering under glasshouse conditions, suitability for production from softwood cuttings in pots, and durable flowers and foliage which make the variety suitable for distribution in the floral and nursery industry.

* * * * *

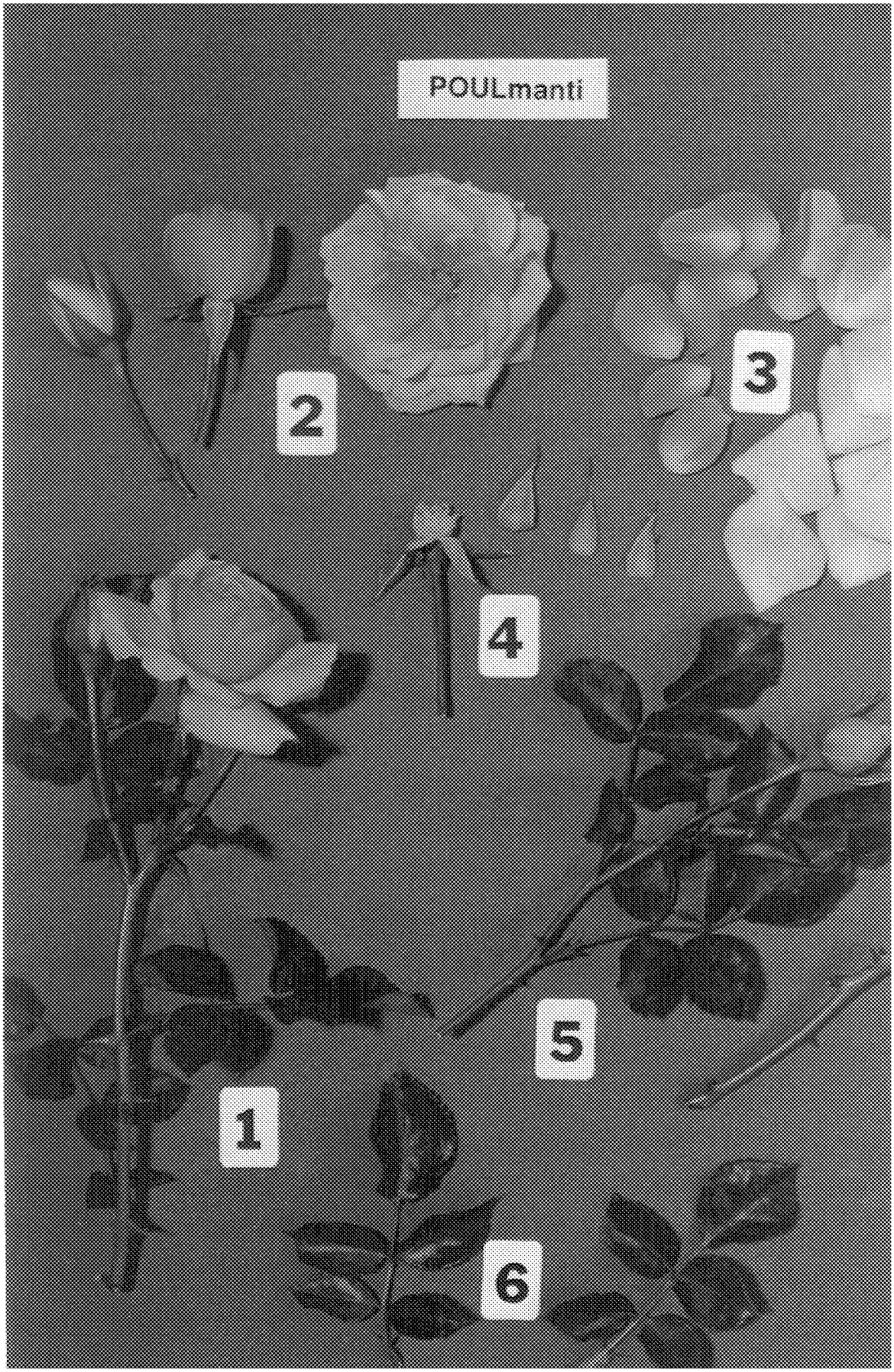
POULmanti
2
3
4
5
1
6